United States Patent [19]
Masterman et al.

[11] Patent Number: 6,007,795
[45] Date of Patent: Dec. 28, 1999

[54] COMPOSITIONS INCLUDING PARTICLES INCLUDING DEGRADABLE MATERIAL AND ANTI-MICROBIAL AGENT

[75] Inventors: Thomas Craig Masterman; Jean L. Spencer, both of Boston, Mass.

[73] Assignee: Gillette Canada Inc., Kirkland, Canada

[21] Appl. No.: 08/783,461

[22] Filed: Jan. 16, 1997

Related U.S. Application Data

[62] Division of application No. 08/322,926, Oct. 13, 1994, Pat. No. 5,616,315.

[51] Int. Cl.$^6$ ..................................................... A61K 7/16
[52] U.S. Cl. ............................... 424/49; 424/52; 424/53; 424/54
[58] Field of Search ...................... 424/49, 52, 53, 424/54, 55, 401; 514/900, 901, 902

[56] References Cited

U.S. PATENT DOCUMENTS

| | | |
|---|---|---|
| Re. 24,899 | 11/1960 | Green . |
| 3,523,906 | 8/1970 | Vrancken . |
| 3,699,979 | 10/1972 | Muhler et al. . |
| 3,934,001 | 1/1976 | Watson . |
| 3,943,949 | 3/1976 | Ashton et al. . |
| 3,957,964 | 5/1976 | Grimm, III . |
| 3,959,457 | 5/1976 | Speaker et al. . |
| 3,991,766 | 11/1976 | Schmitt et al. . |
| 4,033,365 | 7/1977 | Klepak et al. . |
| 4,071,614 | 1/1978 | Grimm, III ............................... 424/49 |
| 4,348,378 | 9/1982 | Kosti . |
| 4,389,330 | 6/1983 | Tice et al. . |
| 4,568,559 | 2/1986 | Nuwayser et al. . |
| 4,622,244 | 11/1986 | Lapka et al. . |
| 4,623,588 | 11/1986 | Nuwayser et al. . |
| 4,685,883 | 8/1987 | Jernberg . |
| 4,780,320 | 10/1988 | Baker ....................................... 424/493 |
| 4,828,955 | 5/1989 | Kasai et al. . |
| 4,837,007 | 6/1989 | Duckworth et al. . |
| 4,861,627 | 8/1989 | Mathiowitz et al. . |
| 4,867,988 | 9/1989 | Chernack . |
| 4,892,736 | 1/1990 | Goodson . |
| 4,904,479 | 2/1990 | Illum . |
| 4,917,892 | 4/1990 | Speaker et al. . |
| 4,919,939 | 4/1990 | Baker ....................................... 424/493 |
| 4,959,220 | 9/1990 | Yamamoto et al. . |
| 4,978,391 | 12/1990 | Jones . |
| 4,980,150 | 12/1990 | Keith . |
| 5,061,106 | 10/1991 | Kent . |
| 5,098,711 | 3/1992 | Hill et al. . |
| 5,211,939 | 5/1993 | Turesky et al. . |
| 5,219,554 | 6/1993 | Groman et al. . |
| 5,225,282 | 7/1993 | Chagnon et al. . |
| 5,250,288 | 10/1993 | Turesky et al. . |
| 5,262,166 | 11/1993 | Liu et al. . |
| 5,281,265 | 1/1994 | Liu . |
| 5,300,290 | 4/1994 | Spencer ..................................... 424/54 |
| 5,382,468 | 1/1995 | Chagnon et al. . |
| 5,447,725 | 9/1995 | Damani et al. .......................... 424/435 |
| 5,614,223 | 3/1997 | Sipos ........................................ 424/489 |
| 5,616,315 | 4/1997 | Masterman et al. ....................... 424/54 |
| 5,779,471 | 7/1998 | Tseng et al. ............................... 433/80 |

FOREIGN PATENT DOCUMENTS

| | | |
|---|---|---|
| 0 244 118 | 4/1987 | European Pat. Off. . |
| 0 244 118 | 11/1987 | European Pat. Off. . |
| WO 92/20319 | 11/1992 | WIPO . |
| WO 93/05680 | 4/1993 | WIPO . |
| WO 93/11754 | 6/1993 | WIPO . |
| WO 94/08562 | 4/1994 | WIPO . |

OTHER PUBLICATIONS

Gref et al., "Biodegradable Long–Circulating Polymeric Nanospheres", *Science*, 263:1600–1603 (Mar., 1994).

Pekarek et al., "Double–walled polymer microspheres for controlled drug release", *Letters to Nature*, 367:258–260 (Jan., 1994).

Müller et al., "In vitro characterization of poly(methyl-methacrylate) nanoparticles and correlation to their vivo fate", *Journal of Controlled Release*, 20:237–246 (1992).

Mathiowitz et al., "Morphology of Polyanhydrine Microsphere Delivery Systems", *Scanning Microscopy*, 4:329–340 (1990), Ratner, "Biomedical Applications of Synthetic Polymers", *Comprehensive Polymer Science*, vol. 7 (1989).

Juliano, "Controlled delivery of drugs: an overview and prospectus", *Drug Delivery Systems* (1980).

*Primary Examiner*—Ralph Gitomer
*Attorney, Agent, or Firm*—Fish & Richardson P.C.

[57] ABSTRACT

A method for inhibiting bacteria in the mouth of a patient which includes placing a particle containing a degradable material and an anti-microbial agent in the mouth of the patient. The exterior of the particle is water-stable. The particles may be coated on dental floss or the bristles of a toothbrush, or incorporated into an oral rinse. Once placed in the mouth, the degradable material degrades to cause release of the anti-microbial agent, resulting in the inhibition of bacteria in the mouth.

34 Claims, No Drawings

COMPOSITIONS INCLUDING PARTICLES INCLUDING DEGRADABLE MATERIAL AND ANTI-MICROBIAL AGENT

This is a divisional of copending application Ser. No. 08/322,926, filed Oct. 13, 1994, now U.S. Pat. No. 5,616,315.

BACKGROUND OF THE INVENTION

The invention relates to systems for delivering anti-microbial agents to the mouth.

Many humans suffer from tooth decay and periodontal disease caused by bacteria in the mouth. As a result, decreasing the number of these bacteria is a problem which has been targeted by members of the dental and health care fields. The most common way of minimizing the number of bacteria is to brush and floss the teeth regularly, and to visit a dental hygienist to have the teeth and gums cleaned thoroughly. Another approach to control bacteria in the mouth is to rinse with a solution containing an effective anti-microbial agent, such as chlorhexidene digluconate.

One of the major side effects of rinsing with a chlorhexidene-based solution is a yellow-brown stain which may develop on the teeth, tongue, and fillings. Although this stain can usually be professionally removed, it is not cosmetically pleasing. In addition to the staining, taste disturbances, such as the perception of sweets and salt, may develop due to the presence of chlorhexidene. In certain patients, scaling and soreness of the oral mucosa may occur. These side effects have been attributed to the high concentration of chlorhexidene (or salt thereof) used in the rinse; it is, therefore, desirable to reduce or control the dosage of chlorhexidene so that anti-microbial effects can be achieved without the onset of undesirable side effects.

SUMMARY OF THE INVENTION

In general, the invention features a method for inhibiting bacteria in the mouth of a patient. The method includes placing a particle containing a degradable material and an anti-microbial agent into the mouth of a patient. The saliva in the mouth causes the degradable material in the particle to degrade, resulting in the release of the anti-microbial agent in a controlled manner over time. The exterior of the particle is water-stable allowing the particles to be incorporated into, for example, aqueous rinses or pastes without the water in the rinse or paste causing the degradable material to degrade prematurely, prior to use.

In one embodiment, the particle is provided with a coating composed of a water-stable material that does not degrade when exposed to one or more enzymes in the mouth. These materials include hydrophobic materials like poly(methyl methacrylate), polystyrene, beeswax, carnauba wax, petroleum wax, or similar materials. The coating is disrupted by mechanical stresses (e.g., brushing, flossing, and chewing); this disruption exposes the underlying degradable material to saliva. As a result, the degradable material degrades, causing the anti-microbial agent to be released.

In another embodiment, the particle is provided with a coating of a water-stable material that degrades when exposed to one or more enzymes in the mouth. Examples of such materials include polyhydroxyalkanoic acid, glycolipids, glycerides, and phospholipids. As the water-stable material degrades by the action of enzymes in the mouth, the underlying degradable material is exposed to saliva and also degrades, resulting in the release of the anti-microbial agent. The water-stable material may also be disrupted by mechanical stresses.

In another embodiment, the particle includes a water-stable material, dispersed throughout the particle, that degrades when exposed to enzymes in the mouth. In this embodiment, the water-stable material (1) functions as the degradable material, and (2) functions to provide the particle with a water-stable exterior. Optionally, the particle may include one or more other degradable materials underneath the water-stable exterior, and also may include one or more other water-stable materials that help provide the water-stable exterior. A preferred material that can be used for this embodiment is glycerol distearate.

Preferred anti-microbial agents include phenolic compounds (monomeric or polymeric, synthetic or natural); nature-derived anti-microbials such as sanguinarine; cetylpyridinium salts; benzalkonium salts; benzethonium salts; domiphen salts; bisbiguanides, such as chlorhexidene; bisbiguanide salts; phosphonium salts; ammonium salts; peroxides and other oxidants; zinc salts; and antibiotics such as penicillin, vancomycin, kanamycin, erythromycin, niddamycin, spiramycin, tetracycline, minocycline, and metronidazole. Particularly preferred anti-microbial agents include chlorhexidene or an acceptable salt of chlorhexidene.

Preferred degradable materials include polyglycolic acid, polylactic acid, and copolymers of glycolic acid and lactic acid, and esters of glycerol.

In some preferred embodiments, the degradable material encapsulates the anti-microbial agent. In other preferred embodiments, the particle is a microsphere, and the diameter of the microsphere is preferably between 0.05 $\mu$m and 100 $\mu$m, more preferably between 0.1 $\mu$m and 30 $\mu$m.

In another aspect, the invention features a toothbrush including a handle and, extending from a portion of the handle, bristles coated with the particles of the invention, or hollow bristles that are partially or totally filled with the particles. In another aspect, the invention features dental floss including an elongated, flexible cord (preferably made of nylon or other durable polymer) coated with the particles of the invention. In still another aspect, the invention features a toothpaste or an oral rinse containing the particles of the invention. The toothpaste generally includes other conventional components such as an abrasive (e.g., silica or alumina, having a particle size of between 5 $\mu$m and 50 $\mu$m), a thickener (e.g., colloidal silica having a particle size of between 0.1 $\mu$m and 1 $\mu$m), and a flavor.

"Encapsulate", as used herein, means that the anti-microbial agent is dispersed throughout or surrounded by the degradable material.

"Degradable material", as used herein, means a material which degrades within three months when placed in the mouth of a typical patient. The materials degrade as a result of exposure to one or more enzymes that commonly are found in the mouth. These enzymes include lipases, proteases, and glucosidases. Specific enzymes include parotid amylase, hyaluronidase, beta-glucuronidase, chondroitin sulfatase, amino acid decarboxylases, catalase, peroxidase (such as lacto peroxidase), collagenase, and lysozyme.

"Water-stable exterior", as used herein, means that the exterior surface of the particle is composed of a material that does not chemically degrade or swell when exposed to water. As a result of the water-stable exterior, substantially no (i.e., less than 5% by weight) anti-microbial agent leaches from the particle when the particle is placed in distilled water (at a concentration of 10% of the dispersion by weight) at room temperature for a month.

"Microsphere", as used herein, means that the particle is substantially spherical in shape.

The particles of the invention can be used to deliver an anti-microbial agent at a predetermined rate for a defined time period. The degradable material essentially allows for continuous inhibition of bacteria in the mouth during the selected time period without necessitating a large initial dosage of the anti-microbial agent. The dosage optionally may be provided in a site-specific manner. The water-stable exterior allows the particles to be stored for a substantial period of time, for example in a mouthwash or a toothpaste.

When chlorhexidene is selected as the anti-microbial agent, the controlled delivery process of the invention results in a reduction of undesirable side effects, such as staining of the teeth and tongue. Significantly, when the particles are composed primarily of a degradable material and an anti-microbial agent, substantially nothing remains of the particles in the mouth or body once the degradable material degrades and all of the anti-microbial agent is released.

DESCRIPTION OF THE PREFERRED EMBODIMENTS

The preferred particles include a degradable material, an anti-microbial agent, and a thin (e.g., less than 10 um) non-porous coating that makes the exterior surface of the particle water-stable.

Preferred degradable materials include polymers such as polycaprolactone, polydecalactone, poly(sebacic anhydride), sebacic acid-co-1,3-bis (carboxyphenoxypropane), sebacic acid-co-1,6-bis (carboxyphenoxyhexane), dedecanoic-co-1,3-bis (carboxyphenoxypropane), dedecanoic-co-1,6-bis (carboxyphenoxyhexane), albumin and derivatives, gelatin and derivatives, starch and derivatives, gum arabic, cellulose and derivatives, polysorbate and derivatives, agarose, lectins, galactose, functionalized nylons (e.g. benzylated), proteins (synthetic and natural), polyorthoesters, polyorthoformate, polyureas, polyurethanes, poly(amide-enamine)s, polyvinylalcohol, polyenolketone (PEK), polyHema, functionalized polyHema, ethylene-vinylacetate copolymers, functionalized polymers and copolymers of lactic and glycolic acid, lactic acid homopolymer, glycolic acid copolymer, copolymers of lactic acid and glycolic acid, polyhydroxybutyrate, poly(ester-imides), functionalized silicones, poly(anhydrides), poly(malic acid), and polyhydroxyalkanoic acid from synthetic or natural sources (bacterial, fungi and the like). Other preferred degradable materials include monomeric species and mixed monomeric/polymeric species such as liposomes, glycolipids, fatty acids, glycerides, carnauba wax, and phospholipids.

The preferred degradable materials can be included in organic/inorganic composites. The composites can include any of the polymers listed above mixed or covalently bound with minerals such as silica, alumina, kaolin, morierite, cordierite, zirconia minerals and the like; any of the monomeric and monomer/polymer species listed above mixed or covalently bound with minerals such as silica, alumina, kaolin, morierite, cordierite, zirconia minerals and the like; proteins bound to silica, titania, and the like; silicon-containing polymers; and polyhydroxyalkanoic acid:salt complexes. The inorganic component(s) of the composite can, for instance, assist in controlling the dosage of anti-microbial agent released in a given period of time, or act as an abrasive if used, e.g., in a toothpaste.

The more preferred degradable materials are polymers such as polyglycolic acid, polylactic acid, and copolymers of glycolic acid and lactic acid, and esters of glycerol. These polymers are well-known and commercially available. For example, polyglycolic acid is available from the American Cyanamid Company (Dexon®) and Polysciences, Inc.; polylactic acid is available from Polysciences, Inc.; and copolymers of glycolic acid and lactic acid are available from American Cyanamid Company (Vicryl®), Ethicon, Inc. (Polyglactin 910) and Polysciences. Alternatively, the polymers can be synthesized according to known procedures. For example, polyglycolic acid can be prepared employing the ring opening polymerization of the dimeric ester of glycolic acid; polylactic acid can be prepared employing the ring opening polymerization of the dimeric ester of lactic acid; and copolymers of glycolic acid and lactic acid can be prepared employing the ring opening polymerization of the corresponding dimeric esters.

Other preferred degradable polymeric materials are commercially available and/or may be prepared by known procedures.

A particularly preferred anti-microbial agent is chlorhexidene, an anti-bacterial compound which contains two biguanide moieties, each attached in the para position to a separate chlorophenyl group, and joined by a hexane linkage (see, for example, Rose et al., J. Chem Soc., p. 4422 (1956) and U.S. Pat. No. 2,684,924). Pharmaceutically acceptable salts of chlorhexidene, such as chlorhexidene gluconate, chlorhexidene diacetate, chlorhexidene dihydrochloride, chlorhexidene dihydrofluoride, and chlorhexidene dihydrobromide may also be used in the present invention. Chlorhexidene and its associated salts are commercially available; the gluconate salt may be purchased, for example, as a 20.5 percent w/w aqueous solution from Pliva Pharmaceutical of Zagreb, Yugoslavia, and from ICI Ltd. of England. Chlorhexidene gluconate as a freeze-dried solid is available from Pliva Pharmaceutical.

Other preferred anti-microbial agents were described previously in the Summary of the Invention and generally, like chlorhexidene digluconate, are commercially available.

The particles preferably include between 1% and 75%, and more preferably between 1% and 25%, of the anti-microbial agent by weight. Too much anti-microbial agent may adversely affect the mechanical strength of the particle, while too little anti-microbial agent may result in an insufficient dosage of the anti-microbial agent being delivered to the mouth.

The thin non-porous (more preferably hydrophobic) coating prevents the anti-microbial agent from leaching from the particle when the particle is stored or incorporated into aqueous systems. Preferred coating materials include poly (methyl methacrylate), polystyrene, beeswax, carnauba wax, petroleum wax, polyhydroxyalkanoic acid, glycolipids, glycerides, phospholipids, and glycerol distearate. The coating materials may be materials (like polystyrene, waxes, or poly(methyl methacrylate) that do not degrade when exposed to enzymes in the mouth, or may be materials (like glycerol distearate, polydroxyalkanoic acid, and other glycerides) that degrade when exposed to enzymes in the mouth. All of these materials are commercially available. Preferably the coating constitutes no more than about 10% of the particle diameter.

The anti-microbial agent may be dispersed throughout the particle along with the degradable material, enclosed within a skin composed of the degradable material, or attached to a skin composed of the degradable material. In the latter embodiment, the degradable material and the anti-microbial agent may have opposite ionic charges and the anti-microbial agent may be adsorbed onto the skin by ionic bonding.

The preferred particles are microspheres that have an average diameter between 0.05 μm and 100 μm, more preferably between 0.1 μm and 30 μm. If the particles are too large they will too easily wash away from oral surfaces and thus will be less likely to settle subgingivally.

The preferred particles can be made by numerous conventional, well-known methods. These include solvent evaporation methods, with or without a surface active agent as necessary, coacervation in all its various forms, pan coating, air-suspension coating, press coating, spray-drying, rotational suspension-separation techniques, melt coating methods, interfacial polymerization, melt-granulation processes and any and all related methods that yield the desired particles as described. Such methods may or may not use organic solvents. Such methods may encapsulate from solution, from the melt or in powdered (solid state) form. Once formed, the particles may be chemically modified (e.g., charged or made magnetic). The particles are then coated with a water stable material. See, for example, the particle-making and particle-coating procedures described generally in Parrott, *Pharmaceutical Technology*, pp. 86–91 (Burgess Pub. Co. 1970); Deasy, *Microencapsulation and Related Drug Procedures*, pp. 1–60 (Marcel Dekker, Inc. 1984); Muller et al., *J. Controlled Release*, 20 (1992): 37–246; Pekarek et al., *Nature*, v. 367 (1994):258–60; Muller et al., *Pharm. Pharmacol. Lett.* v. 3 (1993):67–70; and Juliano (ed.), *Drug Delivery Systems* (Oxford University Press 1980).

The preferred particles can be placed in the mouth of a patient, e.g., by a dental instrument, or can be delivered to the mouth during routine dental hygiene, e.g., using a toothbrush, dental floss, oral rinse or toothpaste. Once the particles are in the oral cavity, they will settle out around the gumline, settle subgingivally, adhere to soft tissue and become immobilized in these areas. The coating can be partially removed during administration of the particles to the mouth, or subsequently during chewing or brushing. If the coating is a material that degrades when contacted with enzymes in the mouth, the coating will additionally (or solely) be removed by degradation after exposure to the enzymes.

Once the particle has settled, various release mechanisms are possible. The operative release mechanism(s) will depend upon the formulation of the particle. Thus, as the degradable material erodes, anti-microbial agent is released. This site-specific release can continue (12 hr to several weeks to several months) until the entire particle is degraded or washed from the mouth or swallowed. If the latter occurs, final degradation will occur in the stomach and/or gastrointestinal tract. Thus, no long term build-up of particles systemically should occur.

The following are examples of the procedures used to make and administer particles of the present invention.

Example 1: Decradable Particles

Degradable particles consisting of poly(DL-lactide)-coglycolide, 80:20, were prepared according to the following procedure:

1. 25 mg poly(DL-lactide)-co-glycolide were dissolved in 2 ml methylene chloride.

2. A 1 wt % solution of polyvinylalcohol (87–89% hydrolyzed) was prepared.

3. The methylene chloride solution was added (all at once) to 30 ml of the 1% polyvinylalcohol solution.

4. The resulting emulsion was vortexed for 1 minute and then sonicated for 1 minute, providing a turbid emulsion.

5. The turbid emulsion was placed in a large-mouthed flask and stirred under medium speed to allow the methylene chloride to evaporate. The resulting white microparticles were allowed to settle, washed with water, and freeze dried. The particles had a particle size of 30–100 um.

Example 2: Coating Degradable Particles

1. The particles from Example 1 were emulsified in 30 ml of 1 wt % polyvinylalcohol solution.

2. 10 mg of polystyrene were dissolved in 2 ml of methylene chloride.

3. The polystyrene solution was added (all at once) to the polyvinylalcohol solution.

4. The resulting emulsion was vortexed for 1 minute and then sonicated for 1 minute, providing a turbid emulsion.

5. The turbid emulsion was placed in a large-mouthed flask and stirred under medium speed to evaporate the methylene chloride. The resulting microparticles were centrifuged, washed, and freeze-dried.

6. The coated particles were viewed using a high-power microscope. The core of degradable material and the polystyrene coating were clearly visible.

Example 3: Degradable Particles Including Chlorhexidene Gluconate 1. 10 mg of chlorhexidene gluconate were added to 5 ml of methylene chloride. The mixture was sonicated to reduce the particle size of the chlorhexidene gluconate. 50 mg of the degradable polymer described in Example 1 were added, and the resulting mixture was vortexed to dissolve the polymer.

2. The methylene chloride solution was added (all at once) to the polyvinylalcohol solution.

3. The resulting emulsion was vortexed for 1 minute and then sonicated for 1 minute, providing a turbid emulsion.

4. The turbid emulsion was placed in a large-mouthed flask and stirred under medium speed to evaporate the methylene chloride. The resulting microparticles were centrifuged, washed, and freeze-dried. The particles then can be coated by the same procedure described in Example 2.

Example 4: Degradable Particles Including Chlorhexidene (Free-Base)

1. 10 mg of chlorhexidene (free-base) were emulsified in 5 ml of methylene chloride. The emulsion was sonicated to reduce particle size of the chlorhexidene.

2. 50 mg of the degradable polymer described in Example 1 were added. The mixture was vortexed to dissolve the polymer.

3. The resulting emulsion was poured into 40 ml of 1% polyvinylalcohol solution, and the resulting mixture vortexed and sonicated, providing a tubid emulsion.

4. The turbid emulsion was placed in a large-mouthed flask and stirred under medium speed to evaporate the methylene chloride. The resulting microparticles were centrifuged, washed, and freeze-dried. The particles then can be coated by the same procedure described in Example 2.

Example 5: Degradable Particles Including Chlorhexidene (Free-Base)

1. 10 mg of chlorhexidene (free-base) were dissolved in 5 ml of ethyl acetate.

2. 50 mg of the degradable polymer described in Example 1 were added. The resulting mixture was vortexed to dissolve the polymer.

3. The resulting solution was poured into 40 ml of 1% polyvinylalcohol solution, and the mixture vortexed and sonicated, providing a turbid emulsion.

4. The turbid emulsion was placed in a large-mouthed flask and stirred under medium speed to evaporate the ethyl acetate. The resulting microparticles were centrifuged, washed, and freeze-dried. The particles then can be coated by the same procedure described in Example 2.

Other embodiments are within the claims. For example, the entire degradable particle can be composed of the anti-microbial agent and a material like glycerol distearate that is water stable but degrades when exposed to mouth enzymes.

What is claimed is:

1. Toothpaste comprising particles comprising a degradable material and an anti-microbial agent, said particles having a water-stable exterior.

2. The toothpaste of claim 1, wherein said anti-microbial agent is chlorhexidene or an acceptable salt thereof.

3. The toothpaste of claim 1, wherein said degradable material is a degradable polymer.

4. The toothpaste of claim 1, wherein said degradable material is selected form the group consisting of polyglycolic acid, polylactic acid, copolymers of glycolic acid and lactic acid, and glycerol distearate.

5. The toothpaste of claim 1, wherein said water-stable exterior is in the form of a non-porous coating comprising a water stable material which does not significantly degrade when contacted with enzymes found in the mouth.

6. The toothpaste of claim 5, wherein said water-stable material is selected from the group consisting of poly (methyl methacrylate), polystyrene, and waxes.

7. The toothpaste of claim 1, wherein said water-stable exterior is in the form of a non-porous coating which degrades when contacted with enzymes found in the mouth.

8. The toothpaste of claim 7, wherein said water-stable exterior comprises glycerol distearate.

9. The toothpaste of claim 1, wherein said degradable material is a material which is water stable.

10. The toothpaste of claim 9, wherein said degradable material comprises glycerol distearate.

11. The toothpaste of claim 1, wherein said anti-microbial agent and said degradable material are dispersed throughout said particles.

12. The toothpaste of claim 1, wherein said anti-microbial agent is enclosed within a skin composed of said degradable material.

13. The toothpaste of claim 1, wherein said anti-microbial agent is attached to a skin composed of said degradable material.

14. The toothpaste of claim 1, wherein said anti-microbial agent has an ionic charge and said degradable material has an ionic charge, the ionic charge of said anti-microbial agent being opposite the ionic charge of said degradable material.

15. The oral rinse of claim 1, wherein said particles are microspheres.

16. The toothpaste of claim 1, wherein said particles have an average diameter between 0.1 $\mu$m and 30 $\mu$m, inclusive.

17. The toothpaste of claim 1, wherein said particles comprise between 1 percent and 75 percent of said anti-microbial agent by weight.

18. An oral rinse suitable for use in oral care, comprising water and particles comprising a degradable material and an anti-microbial agent, said particles having a water-stable exterior.

19. The oral rinse of claim 18, wherein said anti-microbial agent is chlorhexidene or an acceptable salt thereof.

20. The oral rinse of claim 18, wherein said degradable material is a degradable polymer.

21. The oral rinse of claim 18, wherein said degradable material is selected form the group consisting of polyglycolic acid, polylactic acid, copolymers of glycolic acid and lactic acid, and glycerol distearate.

22. The oral rinse of claim 18, wherein said water-stable exterior is in the form of a non-porous coating comprising a water stable material which does not significantly degrade when contacted with enzymes found in the mouth.

23. The oral rinse of claim 22, wherein said water stable material is selected from the group consisting of poly (methyl methacrylate), polystyrene, and waxes.

24. The oral rinse of claim 18, wherein said water-stable exterior is in the form of a non-porous coating which degrades when contacted with enzymes found in the mouth.

25. The oral rinse of claim 24, wherein said water-stable exterior comprises glycerol distearate.

26. The oral rinse of claim 18, wherein said degradable material is a material which is water stable.

27. The oral rinse of claim 26, wherein said degradable material comprises glycerol distearate.

28. The oral rinse of claim 18, wherein said anti-microbial agent and said degradable material are dispersed throughout said particles.

29. The oral rinse of claim 18, wherein said anti-microbial agent is enclosed within a skin composed of said degradable material.

30. The oral rinse of claim 18, wherein said anti-microbial agent is attached to a skin composed of said degradable material.

31. The oral rinse of claim 18, wherein said anti-microbial agent has an ionic charge and said degradable material has an ionic charge, the ionic charge of said anti-microbial agent being opposite the ionic charge of said degradable material.

32. The oral rinse of claim 18, wherein said particles are microspheres.

33. The oral rinse of claim 18, wherein said particles have an average diameter between 0.1 $\mu$m and 30 $\mu$m, inclusive.

34. The oral rinse of claim 18, wherein said particles comprise between 1 percent and 75 percent of said anti-microbial agent by weight.

* * * * *